(12) United States Patent
Buijs et al.

(10) Patent No.: US 6,379,294 B1
(45) Date of Patent: Apr. 30, 2002

(54) PROCESS FOR PREPARING ESTERQUATS

(75) Inventors: Adrianus Buijs; Gerardus Van Gurp, both of Deventer; Tjitte Nauta, Amersfoort; Robert Smakman; Anne Marijke Wit-Van Grootheest, both of Deventer, all of (NL)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 09/618,871

(22) Filed: Jul. 19, 2000

(30) Foreign Application Priority Data

Jul. 29, 1999 (EP) .............................. 99202499

(51) Int. Cl.$^7$ .......................................... C07C 227/00
(52) U.S. Cl. ...................... 584/114; 554/110; 564/295; 564/296
(58) Field of Search .............................. 554/110, 114; 564/295, 296

(56) References Cited

U.S. PATENT DOCUMENTS

| 4,675,131 A | 6/1987 | Walraevens et al. ........ 260/404 |
| 5,523,433 A | 6/1996 | Toney et al. ................. 554/114 |

FOREIGN PATENT DOCUMENTS

| CA | 2256450 | 12/1997 | ......... C07C/219/06 |
| DE | 1 200 290 | 9/1965 | |
| EP | 0 187 298 | 7/1986 | ......... C07C/93/187 |
| WO | WO 96/34177 | 10/1996 | ........... E21B/37/06 |
| WO | WO 97/47588 | 12/1997 | ......... C07C/213/06 |
| WO | 97/47588 | * 12/1997 | |
| WO | WO 99/13197 | 3/1999 | ........... E21B/37/06 |

OTHER PUBLICATIONS

European Search Report, dated Dec. 14, 1999.
International Search Report, dated Oct. 6, 2000.
*Journal Organic Chemistry*, vol. 7, pp. 442–447 (1994), Micellar Catalysis Of Organic Reactions. Part 36. Nucleophilic Aromatic Substitution Reactions In Hydroxy Functionalized Micelles With Bulky Head Groups, Trevor J. Broxton and Mathew Lucas.

*Organic Syntheses*, vol. 2, 1963, pp., 111–112.

*Ullmann's Encyclopedia of Industrial Chemistry*, fifth edition, vol. A8, 1987, pp. 493–504.

IBC, The $2^{nd}$ International Conference on Controlling Hydrates, Waxes And Asphaltenes, Oct. 20 & 21, 1997.

* cited by examiner

*Primary Examiner*—Deborah D. Carr
(74) *Attorney, Agent, or Firm*—Lainie E. Parker

(57) ABSTRACT

A process for preparing an esterquat composition comprising (a) reacting a tertiary amine according to formula I:

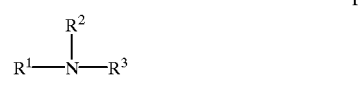

wherein $R^1$ represents a $C_3$–$C_6$ hydrocarbon group, $R^2$ represents a $C_3$–$C_6$ hydrocarbon group, a —$R^4$—OH group or a —$CH_2[CH(OH)]_nCH_2OR^5$ group, if $R^2$ represents a $C_3$–$C_6$ hydrocarbon group, $R^3$ represents a —$R^4$—OH group or a —$CH_2[CH(OH)]_nCH_2OR^5$ group, if $R^2$ represents a —$R^4$—OH group, $R^3$ represents a —$R^4$—OH group or a —$CH_2[CH(OH)]_nCH_2OR^5$ group, if $R^2$ represents a —$CH_2[CH(OH)]_nCH_2OR^5$ group, $R^3$ represents a —$CH_2[CH(OH)]_nCH_2OR^5$ group, $R^4$ represents a $C_2$–$C_4$ hydrocarbon group, n is 1–4, and $R^5$ represents H or a $C_1$–$C_{30}$ hydrocarbon group, with a $C_3$–$C_6$ hydrocarbyl halide or a di($C_3$–$C_6$) hydrocarbyl sulfate, followed by (b) reaction with a $C_8$–$C_{30}$ acid halide, with the proviso that at least one hydroxy group is esterified. Additionally, there are compositions comprising this esterquat and the use of such compositions as a gas hydrate growth inhibitor.

12 Claims, No Drawings

PROCESS FOR PREPARING ESTERQUATS

FIELD OF THE INVENTION

The invention relates to a process for preparing an esterquat, compositions comprising said esterquat, and the use of said compositions as a gas hydrate growth inhibitor.

BACKGROUND OF THE INVENTION

Gas hydrate crystals (clathrates of gases in a lattice consisting of water molecules) are formed in natural gas and crude oil by the interaction of low-boiling hydrocarbons, such as methane, ethane, propane, butane, and isobutane, and water under conditions of elevated pressure and reduced temperature. It has been known for a long time that gas hydrate crystals when allowed to form and grow inside a conduit such as a pipeline, tend to block or even damage the conduit. A number of methods have been suggested to prevent such blocking, of which the use of a crystal growth inhibitor is considered to be very attractive.

Various types of gas hydrate growth inhibitors are known in the art and at present preference is given to quaternary ammonium compounds (i.e. quats) due to their high efficiency. Preferred compounds contain at least one ester function in order to improve the biodegradability of the quat and such compounds are referred to as esterquats. A particularly interesting class of esterquat gas hydrate growth inhibitors are diesterquats.

WO 99/13197 relates to a method for inhibiting the plugging of a conduit by gas hydrates wherein use is made of a quaternary ammonium gas hydrate growth inhibitor. Diesters of dibutyl diisopropanol ammonium bromide and coconut fatty acid and of dibutyl diisobutanol ammonium bromide and coconut fatty acid are described. These diesterquats are prepared, e.g., by quaternizing dibutyl isopropanol amine with propylene oxide and hydrogen bromide in isopropanol, followed by acylation of the dibutyl diisopropanol ammonium bromide formed with coconut fatty anhydride.

Disadvantages of this process are that it proceeds in a low yield, that it requires the use of special equipment, that it uses a solvent, which needs to be removed, and that it uses coconut fatty anhydride, which is not readily available. A further drawback is that during the esterification one equivalent of coconut fatty acid is formed, which needs to be recycled. For these reasons, the process of WO 99/13197 is less attractive economically.

WO 96/34177 discloses the diester of dibutyl diethanol ammonium bromide and coconut fatty acid in Experiment A 2b and the diester of dibutyl diethanol ammonium chloride and tallow fatty acid in Experiment A 3b, but without giving experimental details on the preparation thereof (see page 6, lines 15–18 of WO 96/34177). These diesterquats are used for inhibiting the plugging of conduits by gas hydrates.

U.S. Pat. No. 5,523,433 discloses a process for preparing dialkyl diacyloxyalkyl ammonium compounds in which an alkyl dialkanol amine such as methyl diethanol amine is first esterified with a $C_{12}$–$C_{22}$ fatty acid in the presence of an acid having a $pK_a$ of below 5 such as hypophosphorous acid, followed by reaction with an alkylating agent such as methyl chloride in a solvent to form a diesterquat. It is further disclosed that such diesterquats are useful as fabric softeners.

It was found that the process disclosed in U.S. Pat. No. 5,523,433 works well for the synthesis of dimethyl diesterquats and trimethyl monoesterquats, but not for dialkyl diesterquats such as dibutyl diesterquats and trialkyl monoesterquats such as tributyl monoesterquats, containing $C_8$–$C_{30}$ fatty acyl groups which could only be obtained in relatively low yields. Another drawback is that a solvent is used.

EP-A-0 187 298 discloses a process wherein a trialkanol amine is esterified with an acid chloride and quaternized with a quaternizing agent. According to the description (page 4, lines 14–15), triethanol amine is the preferred tertiary amine. The length of the acyl group of the acid chloride is defined as from 2 to 10 carbon atoms in total, and Examples 1–3 and 4 describe the use of acetyl chloride and octanoyl chloride, respectively. It further discloses that the esterquats have surface-active properties and may be used as detergents. In Example 3 of this document it is described that solid n-butyl tris(2,3-di-hydroxypropyl)ammonium chloride, obtained by reacting bis(2,3-dihydroxypropyl)-n-butyl amine with 1-chloro-2,3-propanediol, was reacted with a 100% excess of acetyl chloride at reflux temperature for 5 hours to 95% completion. The reaction product was dried and subsequently crystallized from a mixture of organic solvents.

Just as U.S. Pat. No. 5,523,433, EP-A-0 187 298 does not relate to the preparation of esterquats in accordance with the present invention such as dibutyl diesterquats and tributyl monoesterquats containing $C_8$–$C_{30}$ fatty acyl groups either.

In view of the prior art discussed above, it was concluded that there is need in the art for an improved, economic route for synthesizing esterquats on a commercial scale.

SUMMARY OF THE INVENTION

The present invention is a process for preparing an esterquat composition comprising (a) reacting a tertiary amine according to formula 1:

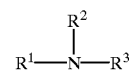

wherein $R^1$ represents a $C_3$–$C_6$ hydrocarbon group, $R^2$ represents a $C_3$–$C_6$ hydrocarbon group, a —$R^4$—OH group or a —$CH_2[CH(OH)]_nCH_2OR^5$ group, if $R^2$ represents a $C_3$–$C_6$ hydrocarbon group, $R^3$ represents a —$R^4$—OH group or a —$CH_2[CH(OH)]_nCH_2OR^5$ group, if $R^2$ represents a —$R^4$—OH group, $R^3$ represents a —$R^4$—OH group or a —$CH_2[CH(OH)]_nCH_2OR^5$ group, if $R^2$ represents a —$CH_2[CH(OH)]_nCH_2OR^5$ group, $R^3$ represents a —$CH_2[CH(OH)]_nCH_2OR^5$ group, $R^4$ represents a $C_2$–$C_4$ hydrocarbon group, n is 1–4, and $R^5$ represents H or a $C_1$–$C_{30}$ hydrocarbon group, with a $C_3$–$C_6$ hydrocarbyl halide or a di($C_3$–$C_6$) hydrocarbyl sulfate, followed by (b) reaction with a $C_8$–$C_{30}$ acid halide, with the proviso that at least one hydroxy group is esterified. Additionally, the invention includes compositions comprising this esterquat and the use of such compositions as a gas hydrate growth inhibitor.

DETAILED DESCRIPTION OF THE INVENTION

As described above, esterquats may be used for inhibiting the plugging of conduits by gas hydrates. Compositions comprising said esterquats need to be transported and pumped through pipelines into the production lines near the gas or oil well. This requires a composition having a high active content with regard to the esterquat, which reduces transportation and storage costs, a low viscosity, which eases pumping, and a solidification temperature lower than −10° C., which ensures handling of the esterquat composition in cold climate areas during winter time.

Surprisingly, a new and efficient process using readily available starting materials and standard production equipment and new esterquat compositions which meet the active content, viscosity, and solidification temperature requirements discussed above were found.

The process according to the present invention for preparing an esterquat composition comprises (a) reacting a tertiary amine according to formula I:

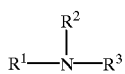

I wherein $R^1$ represents a $C_3$–$C_6$ hydrocarbon group, $R^2$ represents a $C_3$–$C_6$ hydrocarbon group, a —$R^4$—OH group or a —$CH_2[CH(OH)]_nCH_2OR^5$ group, if $R^2$ represents a $C_3$–$C_6$ hydrocarbon group, $R^3$ represents a —$R^4$—OH group or a —$CH_2[CH(OH)]_nCH_2OR^5$ group, if $R^2$ represents a —$R^4$—OH group, $R^3$ represents a —$R^4$—OH group or a —$CH_2[CH(OH)]_nCH_2OR^5$ group, if $R^2$ represents a —$CH_2[CH(OH)]_nCH_2OR^5$ group, $R^3$ represents a —$CH_2[CH(OH)]_nCH_2OR^5$ group, $R^4$ represents a $C_2$–$C_4$ hydrocarbon group, n is 1–4, and $R^5$ represents H or a $C_1$–$C_{30}$ hydrocarbon group, with a $C_3$–$C_6$ hydrocarbyl halide or a di($C_3$–$C_6$) hydrocarbyl sulfate, followed by (b) reaction with a $C_8$–$C_{30}$ acid halide, with the proviso that at least one hydroxy group is esterified.

$R^1$ may be a linear or branched $C_3$–$C_6$ hydrocarbon group. If $R^2$ represents a $C_3$–$C_6$ hydrocarbon group, it may be a linear or branched $C_3$–$C_6$ hydrocarbon group.

$R^4$ independently may be a linear or branched $C_2$–$C_4$ hydrocarbon group. $R^5$ independently may be hydrogen or a linear or branched, saturated or unsaturated $C_1$—$C_{30}$ hydrocarbon group.

Preferably, $R^1$ represents a $C_3$–$C_6$ hydrocarbon group and $R^2$ and $R^3$ both represent a —$R^4$—OH group. More preferably, $R^1$ represents a $C_4$–$C_5$ hydrocarbon group, most preferably an n-butyl group. Preferably, the tertiary amine is reacted with a $C_3$–$C_6$ hydrocarbyl halide, followed by reaction with a $C_8$–$C_{30}$, preferably $C_{10}$–$C_{24}$, more preferably $C_{10}$–$C_{18}$ acid halide.

Preferably, the $C_3$–$C_6$ hydrocarbyl halide is n-butyl bromide and the $C_8$–$C_{30}$ acid halide is cocoyl chloride.

The main product of the process according to the present invention is an esterquat according to formula II:

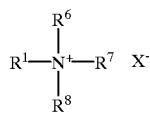

II wherein $R^1$ represents a $C_3$–$C_6$ hydrocarbon group, $R^6$ represents a $C_3$–$C_6$ hydrocarbon group, a —$R^4$—O—$R^9$ group, or a —$CH_2[CH(OR^{10})]_nCH_2OR^{11}$ group, if $R^6$ represents a $C_3$–$C_6$ hydrocarbon group, $R^7$ represents a —$R^4$—O—$R^9$ group or a —$CH_2[CH(OR^{10})]_nCH_2OR^{11}$ group, if $R^6$ represents a —$R^4$—O—$R^9$ group, $R^7$ represents a —$R^4$—O—$R^9$ group or a —$CH_2[CH(OR^{10})]_nCH_2OR^{11}$ group, if $R^6$ represents a —$CH_2[CH(OR^{10})]_nCH_2OR^{11}$ group, $R^7$ represents a —$CH_2[CH(OR^{10})]_nCH_2OR^{11}$ group, $R^4$ represents a $C_2$–$C_4$ hydrocarbon group, $R^9$ represents H or a $C_8$–$C_{30}$ acyl group, $R^{10}$ represents H or a $C_8$–$C_{30}$ acyl group, n is 1–4, $R^{11}$ represents H, a $C_1$–$C_{30}$ hydrocarbon group or a $C_8$–$C_{30}$ acyl group, $R^8$ represents a $C_3$–$C_6$ hydrocarbon group, and $X^-$ represents a halide or a $C_3$–$C_6$ hydrocarbyl sulfate, with the proviso that at least one ester group is present.

The main side-products of the process according to the present invention are $C_3$–$C_6$ ether derivatives and salts thereof formed by alkylation of one or more hydroxyl groups of the tertiary amine and tertiary amine salts formed from unreacted tertiary amine of formula I. As a result, $C_3$–$C_6$ ether derivatives of esterquats of formula II may also be formed.

$R^1$ and $R^4$ have the same meaning as described above. If $R^6$ represents a $C_3$–$C_6$ hydrocarbon group, it may be a linear or branched $C_3$–$C_6$ hydrocarbon group. $R^8$ may be a linear or branched, saturated or unsaturated $C_3$–$C_6$ hydrocarbon group. $R^9$ and $R^{10}$ independently may be hydrogen or a linear or branched, saturated or unsaturated $C_8$–$C_{30}$ acyl group. $R^{11}$ independently may be hydrogen, a linear or branched, saturated or unsaturated $C_1$–$C_{30}$ hydrocarbon group or a linear or branched, saturated or unsaturated $C_8$–$C_{30}$ acyl group.

In a first preferred class of esterquat compounds according to formula II, $R^1$ and $R^8$ both represent a $C_3$–$C_6$ hydrocarbon group, $R^6$ and $R^7$ both represent a —$R^4$—O—$R^9$ group, $R^4$ represents a $C_2$–$C_4$ hydrocarbon group, $R^9$ represents a $C_8$–$C_{30}$ acyl group, and $X^-$ represents a halide ion. These compounds are represented by formula III:

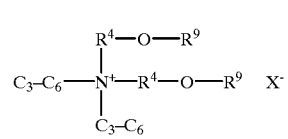

III

Preferably, the sum of the number of carbon atoms present in the two $R^9$ groups is from 20 to 36.

In a more preferred class of esterquats according to formula III, $R^4$ represents a $C_2$–$C_3$ hydrocarbon group and $R^9$ represents a $C_{10}$–$C_{24}$ acyl group, most preferably a $C_{10}$–$C_{18}$ acyl group.

In a second preferred class of esterquat compounds according to formula II, $R^1$, $R^6$, and $R^8$ represent a $C_3$–$C_6$ hydrocarbon group and $R^7$ represents a —$R^4$—O—$R^9$ group, $R^4$ represents a $C_2$–$C_4$ hydrocarbon group, $R^9$ represents a $C_8$–$C_{30}$ acyl group, and $X^-$ represents a halide ion. These compounds are represented by formula IV:

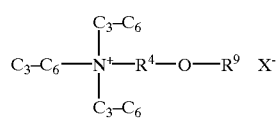

$$\text{IV}$$

In a more preferred class of esterquats according to formula IV, $R^4$ represents a $C_2$–$C_3$ hydrocarbon group and $R^9$ represents a $C_{12}$–$C_{24}$ acyl group.

In a third preferred class of esterquat compounds according to formula II, $R^1$, $R^6$, and $R^8$ represent a $C_3$–$C_6$ hydrocarbon group and $R^7$ represents a $CH_2[CH(OR^{10})]_nCH_2OR^{11}$ group, $R^{10}$ represents H or a $C_8$–$C_{30}$ acyl group, $R^{11}$ represents H, a $C_1$–$C_{30}$ hydrocarbon group or a $C_8$–$C_{30}$ acyl group, n is 1–4, and $X^-$ represents a halide ion. At least one ester group should be present. These compounds are represented by formula V:

$$\text{V}$$

When neither $R^{10}$ nor $R^{11}$ represent H, it is preferred that the sum of the number of carbon atoms present in $R^{10}$ and $R^{11}$ is from 20 to 36.

In a more preferred class of esterquats according to formula V, n is 1 and $R^{10}$ and $R^{11}$ both represent a $C_{10}$–$C_{24}$ acyl group, most preferably a $C_{10}$–$C_{18}$ acyl group.

In the structures of the esterquats according to formulae III–V, the $C_3$–$C_6$ hydrocarbon group preferably is a $C_4$–$C_5$ group, most preferably it represents an n-butyl group.

Either a single tertiary amine or a mixture of tertiary amines according to formula I may be used as the starting material in the invention process.

The invention process can be carried out using means and standard production equipment well-known to a person skilled in the art.

Step (a) of the invention process, i.e. the quaternization reaction, typically is carried out at a temperature of from 60° C. to 120° C. for a period of time of from 2 to 10 days.

It was found that with alkyl halides like butyl halides, the bromides gave a satisfactory selectivity and yield, whereas the corresponding chlorides gave a poor selectivity and low yield. For example, this was the case for the quaternization of N-n-butyl diisopropanol amine with n-butyl bromide as compared to quaternization with n-butyl chloride.

Further, it was observed that the selectivity to quats of the quaternization reaction is lower at higher temperatures, the main side-reaction being ether formation. The by-products formed are of the formulae I–II wherein one or more of the hydroxyl groups are transformed into $C_3$–$C_6$ hydrocarbyl ether groups. In addition, as a by-product the hydrogen halide or $C_3$–$C_6$ hydrocarbyl sulfuric acid salt of the tertiary amine starting material and/or ether derivatives thereof may be formed. So, it is preferred to determine the lowest temperature at which conversion takes place at an acceptable rate without causing solidification (see below) of the reaction mixture and to perform the reaction at that temperature. In general, the by-products need not be removed from the reaction mixture of step (a).

Preferably, use is made in the invention process of a $C_3$–$C_6$ hydrocarbyl halide. Most preferably, n-butyl bromide is used.

It is preferred to use an essentially stoichiometric amount of the $C_3$–$C_6$ hydrocarbyl halide. This yields optimum selectivity and reaction rate.

It further is preferred to carry out the quaternization reaction essentially in the absence of a solvent.

It was found that when carrying out the quaternization of N-n-butyl diisopropanol amine with an equimolar amount of n-butyl bromide in the absence of a solvent, some of the reaction product solidified during the reaction (at the reaction temperature). This solidification could be prevented by replacing at least 5 mole %, preferably 5–50 mole %, more preferably 5–20 mole %, of the amount of N-n-butyl diisopropanol amine with N-n-butyl diethanol amine. Solidification can also be prevented by replacing at least 10 mole %, more preferably 10–40 mole %, of the amount of N-n-butyl diisopropanol amine with N-n-butyl isopropanol ethanol amine as the starting tertiary amine. The person skilled in the art will recognize that these measures may also be applied to other tertiary amine starting materials in case solidification of the reaction mixture occurs.

Typical examples of suitable tertiary amines include N-n-butyl diethanol amine, N-n-butyl diisopropanol amine, N-n-butyl ethanol isopropanol amine, N-n-butyl ethanol sec-butanol amine, di-N-n-butyl 2,3-dihydroxypropyl amine, N-n-pentyl diisopropanol amine, N-n-pentyl diethanol amine, tertiary amines of the formula $Bu_2NCH_2CH(OH)CH_2OR^5$, wherein $R^5$ represents a $C_1$–$C_{30}$ hydrocarbon group, $(Bu)(HOCH_2CH_2)NCH_2CH(OH)CH_2OR^5$, wherein $R^5$ represents H or a $C_1$–$C_{30}$ hydrocarbon group, and mixtures thereof. Preferably, the tertiary amine comprises N-n-butyl diisopropanol amine.

Typical examples of suitable $C_3$–$C_6$ hydrocarbyl halides include n-butyl bromide, n-pentyl bromide, allyl chloride, and mixtures thereof.

A typical example of a suitable di($C_3$–$C_6$) hydrocarbyl sulfate is di-n-butyl sulfate.

Methods for preparing symmetrical and unsymmetrical dialkyl sulfates are known to the person skilled in the art, e.g., see *Organic Syntheses*, Collective Volume 2, John Wiley & Sons, Inc., New York, pages 111–112, Ullman's *Encyclopedia of Industrial Chemistry*, Fifth Edition, Volume A8, VCH, Dialkyl sulfates and alkylsulfuric acids, K. Weisenberger and D. Mayer, pages 493–503, and DE 1200290.

The product of step (a) of the invention process can be used in step (b) with or without purification. If desired, the intermediate product may be (re)crystallized from a suitable solvent such as acetone, 2-butanone, and 4-methyl-2-pentanone. Preferably, no purification of the intermediate quaternary ammonium product is carried out.

Step (b) of the invention process, i.e. the esterification reaction, is carried out by contacting the reaction product of step (a) with a $C_8$–$C_{30}$ acid halide. Typically, step (b) is carried out in the absence of a solvent or a scavenger. A scavenger, in the form of an amine, typically is used in the art to capture the hydrogen halide formed during esterification.

In a typical reaction, the acid halide, normally an acid chloride, is dosed at such a rate that the evolution of acid, typically hydrochloric acid, is controlled. Typically, the esterification is carried out at a temperature of 20 to 110° C. for a period of time of 0.5 to 5 h. For example, for the esterification of a mixture of di-n-butyl diisopropanol ammonium bromide and di-n-butyl diethanol ammonium bromide with cocoyl chloride the esterification temperature is kept between 95 and 100° C. for about 2 h. The hydrochloric acid which evolves from the reaction mixture preferably is captured in a caustic scrubber.

It was found that the esterification products containing residual hydrogen halide remained pourable down to ambient temperature and did not require dilution with a solvent. As a result, the esterification in accordance with the present invention can be carried out with a highly efficient use of the reactor volume (i.e. a high space-time yield), leading to an economic process.

The $C_8$–$C_{30}$ acid halide preferably is derived from a readily available fatty acid, such as coconut fatty acid and tallow fatty acid, with coconut fatty acid being most preferred, using methods that are known to one of ordinary skill in the art.

The acid remaining in the reaction product of step (b) of the invention process preferably is neutralized, because it causes hydrolysis of the ester groups and corrosion of the equipment used. As is known to the person skilled in the art, this can be achieved in a number of ways. For example, use can be made of an organic base such as an amine, an inorganic base such as an alkali metal hydroxide or of a basic ion-exchange resin. Neutralization can be carried out after completion of or even during the esterification reaction as described below.

In one embodiment for carrying out the neutralization, the esterification reaction is run to completion and then the reaction mixture is diluted with a water-immiscible liquid which is a solvent for the esterquat and which allows phase separation. This solution is contacted with an aqueous solution containing 5–50 wt %, preferably 5–25 wt %, of an alkali metal hydroxide at a temperature of 10–90° C., keeping a pH of 1–10, followed by separating the organic phase and, if desired, isolating the neutralized esterquat. Any amine salts formed during step (a) of the invention process (see above) are simultaneously converted into the corresponding free amines.

Preferably, for the neutralization an aqueous sodium hydroxide, i.e. caustic, solution is used.

Suitable water-immiscible solvents include aliphatic and aromatic hydrocarbons, ethers, and ketones. Typical examples include toluene, cumene, Shellsoll® AB, Shellsoll® N, Solvesso® 150, Solvesso® 200, Kemelix® 610, 4-methyl-2-pentanone, 2,6-dimethyl-4-heptanone, and cyclohexanone. Of these, ketones like 4-methyl-2-pentanone, 2,6-dimethyl-4-heptanone, and cyclohexanone are preferred.

The use of ketone solvents not only leads to an optimum result in the neutralization procedure, but the product solution obtained after neutralization also meets the various requirements set for formulations which are to be stored, transported, and used for inhibiting the growth of gas hydrates, notably with regard to cost of the formulation, safety (e.g. flash point), product solubility (e.g. solidification temperature), ease of transportation (e.g. viscosity), cost of transportation, storage stability, and ecotoxicity.

Preferably, in this embodiment of the neutralization a heel of an alkali metal salt solution, e.g., an aqueous sodium chloride solution, is provided, and then the organic phase (with the water-immiscible solvent) and the aqueous alkali metal hydroxide solution are added to the heel simultaneously. During neutralization the pH preferably is kept between 3 and 6, more preferably 3 and 5, in order to prevent ester hydrolysis, and the flows of the organic phase and the alkali metal hydroxide solution are adjusted accordingly. Below 50–60° C. emulsification of the reaction mixture may occur, hence the temperature at which neutralization is carried out preferably is kept at 60–80° C. Higher temperatures may cause too much hydrolysis of the ester groups.

The neutralization procedure can be carried out batchwise or continuously. It was found that neutralization could be carried out continuously either in one stirred tank or in two stirred tanks connected in series (see Examples).

In another embodiment of the neutralization procedure, the acid is neutralized by the addition of a sufficient amount of an organic base in the form of an amine, preferably a tertiary amine. As a result, the salt of the amine added is formed. The ratio between the (tertiary) amine added and the esterquat according to formula II can be controlled by evaporation of the acid, e.g., stripping of hydrochloric acid, from the crude reaction mixture.

In this embodiment, the amine can be added after completion of the esterification reaction or even during the esterification reaction. Preferably, it is added after completion of the esterification reaction. In this case, the amine may be added as such, e.g. ammonia, or in the form of an aqueous solution thereof, e.g. an aqueous ammonium hydroxide solution.

If desired, a small amount of a solvent, typically in an amount of 10 to 20 wt % based on the total weight of the mixture, can be used in order to improve the handling of the reaction product. The solvent can be added before or after neutralization with the amine. Any solvent may be used for this purpose.

Suitable solvents include the water-immiscible solvents that are mentioned above.

The tertiary amine preferably contains at least two $C_3$–$C_6$ hydrocarbon groups, at least two $C_3$–$C_6$ hydroxy-containing hydrocarbon groups or at least one $C_3$–$C_6$ hydrocarbon group and one $C_3$–$C_6$ hydroxy-containing hydrocarbon group. The third group on the tertiary amine may be a $C_1$–$C_{30}$ hydrocarbon group, optionally containing a hydroxy or ester group.

Typical examples of suitable tertiary amines include tri-n-butyl amine, di-n-butyl coco amine, and di(2-hydroxybutyl) coco amine.

This particular embodiment has the advantage that no waste water is generated and that the use of a solvent can be avoided. Moreover, it was found that salts of tertiary amines like tri-n-butyl amine and di-n-butyl decyl amine as such inhibited the growth of gas hydrates (see U. C. Klomp, V. Kruka, and R. Reijnhart, Low-dosage inhibitors: (how) do they work?, Proceedings of IBC Conference *Controlling Hydrates, Waxes, and Asphaltenes,* 20–21 October 1998, Aberdeen).

The present invention further relates to a composition comprising one or more esterquats of formula II as defined above, obtained by the process described above, and a ketone solvent as defined above.

The present invention also relates to a composition comprising one or more esterquats of formula 11 as defined above, obtained by the process described above, an amine salt, preferably a tertiary amine salt, as defined above and optionally a solvent as defined above.

Preferably, the compositions in accordance with the present invention comprise at least 30 wt %, more preferably at least 50 wt %, most preferably at least 70 wt %, of the esterquat, based on the total weight of the composition.

In a preferred embodiment of the compositions in accordance with the present invention, the composition further comprises 0.01–10 wt %, preferably 0.1–5 wt %, more preferably 1–3 wt %, of water, which acts as a co-solvent, based on the total weight of the composition, i.e. the organic phase. This amount of water may already be present after having carried out the neutralization procedure, or if it is not present in a sufficient amount, it may be added afterwards.

It was found that the presence of water provided a formulation having a reduced viscosity as well as a reduced solidification temperature while still providing a good hydrolytic stability of the esterquat. The presence of 1–3 wt % of water can compensate for about 10 wt % of solvent with respect to the viscosity of the formulation. This effect is even more pronounced with respect to the solidification temperature. This allows the production of formulations of a certain viscosity having a higher esterquat active content than formulations which do not contain a water co-solvent. Being able to manufacture high active content formulations reduces costs with respect to the amount of solvent to be used, storage, and transport.

The present invention also relates to the use of the compositions described above for gas hydrate growth inhibition.

The present invention is illustrated by the following examples.

EXAMPLE 1

A 5-liter autoclave was flushed with nitrogen and N-n-butyl diisopropanol amine (BDIPA, 1,805 g, 9.55 moles), N-n-butyl diethanol amine (BDEA, 176 g, 1.09 moles), and n-butyl bromide (1,471 g, 10.73 moles) were charged to the reactor at ambient temperature. The reactor was closed and heated to 100° C. in 1 h. The reaction was completed after a reaction time of 120 h. The pressure was allowed to build up during the reaction to a value of approx. 1 bar (i.e. $10^5$ Pa) overpressure. A sample showed that the amine conversion was >95% and the selectivity to quaternized product was >70%. This product was used without further purification.

N-n-butyl diisopropanol amine was prepared by adding two mole equivalents of propylene oxide to one mole equivalent of n-butyl amine in a reactor heated to 125° C., while keeping the pressure at $3\times10^5$ to $5\times10^5$ Pa and raising the temperature to 175°0 C. as soon as most of the n-butyl amine was converted to n-butyl isopropanol amine. After a reaction time of 4 to 8 h, N-n-butyl diisopropanol amine in a yield of 99% or higher was obtained.

N-n-butyl diethanol amine was prepared in an analogous way.

EXAMPLE 2

In a reactor set-up similar to that in Example 1, BDIPA (945 g, 5 moles) and n-butyl bromide (692 g, 5 moles) were charged to the reactor. This mixture was heated to 100° C. in 1 h and kept at that temperature for 125 h. An amount of 1,625 g of product was obtained with an approx. 70% yield of di-n-butyl diisopropanol ammonium bromide. Amine conversion was 93% and the selectivity to quaternized product was 71%. This product was purified as follows.

In a 1.5-liter stirred reaction vessel an amount of 305 g of hot product was poured into 600 g of 2-butanone at ambient temperature and the whole was stirred for 1 h. The temperature increased to 40° C. A slurry of white crystals was obtained. After one night at ambient temperature, this mixture was cooled down in 2 h with stirring. After filtration and washing of the filter cake with 2-butanone and removal of the adhering solvent by evaporation, an amount of 151 g of white crystals of di-n-butyl diisopropanol ammonium bromide with a purity of approx. 99% and having a melting range of 131–133° C. was obtained.

EXAMPLE 3

To a reactor equipped with a jacket for heating or cooling and a stirrer the product of Example 1 (566 g, 1.75 moles) was charged at a temperature of 100° C. Then, at ambient pressure, 688 g (3 moles) of cocoyl chloride were dosed in 52 min, the temperature being kept between 95 and 100° C. HCl which evolved from the reaction mixture was captured in a caustic scrubber system. A sample was taken after a post-reaction time of 60 min. NMR analysis showed a degree of esterification of the alcohol functions of >98%. The yield was 1200 g.

EXAMPLE 4

An amount of 150 g of the product of Example 3, having a residual HCl content of 1.53 mmoles/g of product was loaded into a reactor equipped with a stirrer at 30° C. Then an amount of 44.5 g of tri-n-butylamine (TBA; 5% molar excess) was added in 30 min, which raised the temperature to 45° C. due to the heat of neutralization. The reaction mixture containing the neutralized esterquat was a homogeneous viscous liquid.

EXAMPLE 5

An amount of 924 g of the product of Example 3 was diluted with 924 g of toluene. This solution contained 0.80 mmole HCl/g and 0.28 mmole tertiary amine. HBr/g.

An amount of 211 g of an aqueous 12 wt % NaCl solution was charged to a 1-liter reactor equipped with provisions for temperature and pH control and a stirrer. The temperature was kept at 70° C. To this solution the above esterquat solution in toluene and an aqueous 2 M NaOH solution were added simultaneously, under well-agitated conditions, in 3 portions, in 25 min, with the pH being kept in the range of 4.9–5.1 and the temperature between 70 and 72° C. After a post-reaction time of 5 min, a phase separation was performed. A total amount of 1,773 g of neutralized esterquat solution was obtained, which after evaporation of the toluene gave 795 g of solid solvent-free esterquat product with an esterquat content of 1.10 mmoles/g and a tertiary amine content of 0.45 mmole/g.

EXAMPLE 6

An amount of 549 g of the product of Example 3 was diluted with 595 g of Shellsol® AB. An amount of 147 g of an aqueous 12 wt % NaCl solution was charged to a 1-liter reactor equipped with provisions for temperature and pH control and a stirrer. Following the procedure described in Example 5 (except that the solvent was not removed), an amount of 1,036 g of neutralized esterquat solution was obtained having an esterquat content of 0.45 mmole/g and a tertiary amine content of 0.22 mmole/g.

EXAMPLE 7

An amount of 210 g of the product of Example 3 was diluted with 90.1 g of 4-methyl-2-pentanone.

An amount of 133.6 g of an aqueous 10 wt % NaCl solution was charged to a 1-liter reactor equipped with provisions for temperature and pH control and a stirrer. An amount of 292 g of this solution was neutralized following the procedure of Example 5. An amount of 280 g of a low-viscous, clear, neutralized esterquat solution was obtained having an esterquat content of 0.70 mmole/g and a tertiary amine content of 0.23 mmole/g.

Similar results were obtained using 2,6-dimethyl-4-heptanone and cyclo-hexanone as diluents.

EXAMPLE 8

A set-up was made of two stirred tank reactors of 80 ml each in series, where the first one flows over into the second one and the second one flows over into a phase separation device. At the start both reactors were loaded with an aqueous 20 wt % NaCl solution (129 g). An amount of 449 g of the esterquat product of Example 3 was diluted with 1,347 g of toluene. This solution (containing 0.417 mmole HCl/g) was fed to the first reactor simultaneously with an alkaline brine solution containing 0.4 mmole NaOH/g and 20 wt % NaCl (total amount 1,766 g). The residence time of both streams was approx. 6 min. The pH in the first reactor was kept between 4 and 5, while maintaining a constant esterquat feed rate and adjusting the rate of the alkaline brine solution. The outlet of the first reactor dropped into the second (post-reaction) reactor, which provided a residence time of 5–6 min in order to complete the neutralization reaction. The pH of the second reactor was kept between 5 and 5.5; an additional amount of 271 g of alkaline brine solution with 0.097 mmole NaOH /g was required to maintain this pH. After 6 h and 25 min and after phase separation, 1,579 g of the organic product phase were obtained. After solvent removal, an amount of 374 g having an esterquat content of 0.92 mmole/g and a tertiary amine content of 0.48 mmole/g was obtained.

The neutralization temperature was maintained between 20 and 30° C. in this Example, but it has to be emphasized that it is likely that a temperature of about 70° C., as mentioned in Example 5 for the batch process, will have to be used on a larger scale (>10 liter) in order to have feasible phase separation efficiency.

EXAMPLE 9

Formulations were made of the reaction products of Examples 4 and 5 in various solvents, with or without the addition of water. Of these formulations, the viscosity at 0° C. and the appearance, i.e. liquid, liquid/solid or solid, at 0° C., −10° C., and −20° C. were determined. The latter parameter gives a rough indication of the solidification temperature of the formulation. The results are shown in Tables 1–3.

TABLE 1

Formulations in various solvents with water as co-solvent

| Exp. | Cpd (wt %) | Solvent[1] (wt %) | Water (wt %) | Viscosity[2] (mPa · s) |
|---|---|---|---|---|
| Compound is the product of Example 4 | | | | |
| 1 | 60 | A, 40 | 0 | 2187 |
|   | 60 | A, 39 | 1 | 525 |
|   | 60 | A, 38 | 2 | 396 |
| 2 | 60 | C, 40 | 0 | 817 |
|   | 60 | C, 38 | 2 | 442 |
|   | 60 | C, 37 | 3 | 335 |
| 3 | 75 | C, 25 | 0 | 1570 |
|   | 75 | C, 22 | 3 | 531 |
|   | 75 | C, 20 | 5 | 409 |

TABLE 2

| Exp. | Cpd (wt %) | Solvent[1] (wt %) | Water (wt %) | Viscosity[2] (mPa · s) |
|---|---|---|---|---|
| Compound is the product of Example 5 | | | | |
| 4 | 30 | A, 70 | 0 | 29 |
|   | 40 | A, 60 | 0 | 100 |
|   | 40 | A, 57 | 3 | 41 |

TABLE 2-continued

| Exp. | Cpd (wt %) | Solvent[1] (wt %) | Water (wt %) | Viscosity[2] (mPa · s) |
|---|---|---|---|---|
| 5 | 50 | A, 50 | 0 | 332 |
|   | 60 | A, 40 | 0 | 1318 |
|   | 60 | A, 37 | 3 | 263 |
| 6 | 50 | B, 50 | 0 | 65 |
|   | 60 | B, 40 | 0 | 177 |
|   | 57 | B, 40 | 3 | 65 |
| 7 | 50 | C, 50 | 0 | 58 |
|   | 65 | C, 35 | 0 | 243 |
|   | 70 | C, 25 | 5 | 220 |
|   | 75 | C, 25 | 0 | 459 |
|   | 75 | C, 22 | 3 | 336 |
| 8 | 75 | D, 25 | 0 | 155 |
|   | 75 | D, 22 | 3 | 112 |
|   | 75 | D, 20 | 5 | 99 |

[1]A is Shellsol ® AB, B is toluene, C is 2,6-dimethyl-4-heptanone, D is cyclohexanone.
[2]The viscosity was determined at 0° C., using a Brookfield Cone-plate LVDVII CP52 viscosity meter.

TABLE 3

Appearance of formulations as a function of temperature[1]

| | | Water content | | | | | |
|---|---|---|---|---|---|---|---|
| | Cpd[3] | 0 wt % | | | 3 wt % | | |
| Temp. (° C.) | (wt %) | 0 | −10 | −20 | 0 | −10 | −20 |
| Solvent[2] | | | | | | | |
| A | 90 | 1 | 1 | 1 | 0 | 1 | 1 |
|   | 80 | 1 | 1 | 1 | 0 | 0 | 1 |
|   | 70 | 0 | 1 | 1 | 0 | 0 | 0 |
|   | 60 | 0 | 0 | 1 | 0 | 0 | 0 |
|   | 50 | 0 | 0 | 1 | 0 | 0 | 0 |
| C | 90 | 1 | 1 | 1 | 0.5 | 1 | 1 |
|   | 80 | 0 | 1 | 1 | 0 | 0 | 1 |
|   | 70 | 0 | 0.1 | 1 | 0 | 0 | 0.2 |
|   | 60 | 0 | 0.1 | 0.1 | 0 | 0 | 0.1 |
| E | 90 | 0 | 1 | 1 | 0 | 0 | 1 |
|   | 80 | 0 | 0.1 | 1 | 0 | 0 | 0.3 |
|   | 70 | 0.2 | 0.2 | 0.2 | 0 | 0 | 0.2 |
|   | 60 | 0.2 | 0.2 | 0.2 | 0 | 0 | 0.1 |

[1]Appearance: 0 is liquid 0–1 is liquid/solid mixture (e.g. 0.2 = 20% of volume is solid), 1 is solid.
[2]A is Shellsol ® AB, C is 2,6-dimethyl-4-heptanone, E is 4-methyl-2-pentanone. The weight percentage solvent used is the balance taking the amounts of cpd and water into account.
[3]Cpd is the product of Example 5

The results given in Tables 1–3 show that the compositions in accordance with the present invention have the desired high active content, low viscosity, and low solidification temperature. The addition of a few percent of water to esterquat formulations resulted in a considerable reduction of the viscosity and a lowering of the solidification temperature.

What is claimed is:
1. A process for preparing an esterquat composition comprising
(a) reacting a tertiary amine according to formula I:

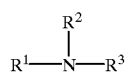

I wherein

R$^1$ represents a C$_3$–C$_6$ hydrocarbon group,

R$^2$ represents a C$_3$–C$_6$ hydrocarbon group, a —R$^4$—OH group or a —CH$_2$[CH(OH)]$_n$CH$_2$OR$^5$ group, if R$^2$ represents a C$_3$–C$_6$ hydrocarbon group, R$^3$ represents a —R$^4$—OH group or a —CH$_2$[CH(OH)]$_n$CH$_2$OR$^5$ group, if R$^2$ represents a —R$^4$—OH group, R$^3$ represents a —R$^4$—OH group or a —CH$_2$[CH(OH)]$_n$CH$_2$OR$^5$ group, if R$^2$ represents a —CH$_2$[CH(OH)]$_n$CH$_2$OR$^5$ group, R$^3$ represents a —CH$_2$[CH(OH)]$_n$CH$_2$OR$^5$ group, R$^4$ represents a C$_2$–C$_4$ hydrocarbon group, n is 1–4, and R$^5$ represents H or a C$_1$–C$_{30}$ hydrocarbon group, with a C$_3$–C$_6$ hydrocarbyl halide or a di(C$_3$–C$_6$) hydrocarbyl sulfate, followed by (b) reaction with a C$_8$–C$_{30}$ acid halide, with the proviso that at least one hydroxy group is esterified.

2. A process according to claim 1, wherein R$^1$ represents a C$_3$–C$_6$ hydrocarbon group and R$^2$ and R$^3$ both represent a —R$^4$—OH group.

3. A process according to claim 1, wherein the tertiary amine is N-n-butyl diisopropanol amine.

4. A process according to claim 3, wherein 5–20 mole % of the N-n-butyl diisopropanol amine is replaced by N-n-butyl diethanol amine or that 10–40 mole % of the N-n-butyl diisopropanol amine is replaced by N-n-butyl isopropanol ethanol amine.

5. A process according to claim 1, wherein step (a) essentially is carried out in the absence of a solvent.

6. A process according to claim 1, wherein the C$_3$–C$_6$ halide is n-butyl bromide and the C$_8$–C$_{30}$ acid halide is cocoyl chloride.

7. A process according to claim 1, wherein the process further comprises neutralizing the reaction product of step (b) and isolating the organic phase.

8. A process according to claim 7, further comprising diluting the reaction product of step (b) with a water-immiscible solvent, and contacting the resulting solution with an aqueous solution of an alkali metal hydroxide.

9. A process according to claim 7, wherein the water-immiscible solvent is a ketone solvent.

10. A process according to claim 7, wherein neutralization of the reaction product of step (b) is carried out by the addition of a sufficient amount of an amine, optionally using a small amount of a solvent.

11. A process according to claim 10, wherein the amine added during the neutralization of the reaction product of step (b) is a tertiary amine.

12. A process according to claim 7, wherein the organic phase comprises 0.01–10 wt % of water.

* * * * *